(12) United States Patent
Mann et al.

(10) Patent No.: US 10,085,451 B2
(45) Date of Patent: *Oct. 2, 2018

(54) SYNERGISTIC HERBICIDAL COMPOSITION CONTAINING PENOXSULAM AND BENTAZON

(71) Applicant: Dow AgroSciences LLC, Indianapolis, IN (US)

(72) Inventors: Richard K. Mann, Franklin, IN (US); Yi-hsiou Huang, Pingtung (TW)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/383,289

(22) Filed: Dec. 19, 2016

(65) Prior Publication Data

US 2017/0094973 A1    Apr. 6, 2017

Related U.S. Application Data

(63) Continuation of application No. 13/219,788, filed on Aug. 29, 2011, now abandoned.

(60) Provisional application No. 61/378,130, filed on Aug. 30, 2010.

(51) Int. Cl.
*A01N 43/90* (2006.01)
*A01N 43/88* (2006.01)

(52) U.S. Cl.
CPC ............. *A01N 43/90* (2013.01); *A01N 43/88* (2013.01)

(58) Field of Classification Search
CPC ................................ A01N 43/90; A01N 43/88
See application file for complete search history.

(56) References Cited

U.S. PATENT DOCUMENTS

| | | | |
|---|---|---|---|
| 5,858,924 A | 1/1999 | Johnson | |
| 8,785,351 B2 * | 7/2014 | Mann | A01N 43/88 504/132 |
| 2006/0167018 A1 | 7/2006 | Zagar et al. | |
| 2006/0183637 A1 | 8/2006 | Loughner et al. | |

FOREIGN PATENT DOCUMENTS

| | | |
|---|---|---|
| CN | 101647450 | 2/2010 |
| CN | 103798255 | 5/2014 |
| CN | 103875686 | 6/2014 |
| EA | 013547 | 6/2010 |
| EP | 0448723 A1 | 10/1991 |
| EP | 2106697 | 10/2009 |
| JP | 59020206 | 2/1984 |
| JP | 03215404 A | 9/1991 |
| JP | 032154404 | 9/1991 |
| JP | 2001233718 | 8/2001 |
| RU | 235746 | 6/2009 |
| SU | 1528327 | 12/1989 |
| WO | 2002/078442 | 10/2002 |
| WO | 2004/080171 | 9/2004 |
| WO | 2006/086640 | 8/2006 |
| WO | 2007/042447 | 4/2007 |
| WO | 2007/101587 | 9/2007 |
| WO | 2008/075743 | 6/2008 |
| WO | 2010059671 A2 | 5/2010 |

OTHER PUBLICATIONS

Lee et al., "Weed Control by Herbicide Mixtures of Ponoxsulam SC in Transplanted Rice Paddy Fields", Korean Journal of Weed Science, 2006, 26(3), pp. 246-253.
Dalamas et al., "Control of Early Watergrass (*Echinochloa oryziodes*) and Late Watergrass (*Echinochloa phyllopogon*) with Cyhalofpo, Clefoxydim, and Penoxsulam Applied Alone and in Mixture with Broadleaf Herbicides", Weed Technology, 2006 24(4), pp. 992-998.
Hwang et al., "Herbicidal efficacy of Flucetosulfuron + Pyrazosulfuron-Ethyl in Controlling Perennial Sedges and Sulfonylurea Resistant Weeds", The korean Journal of Pesticide Science, 2006, 10(4), pp. 320-328.
Weed Management in Rice. [online] Department of Plant Science, 2008 [retrieved onJan. 21, 2015] <http://web.archive.org/web/20080320012054/http://http://natres.psu.ac.th/Department/PlantScience/510-111web/Technology%20Changes_Rice/08.weed_management_in_rice.html>.
Benzaton. Pesticide Information Profile. [online] Extension Toxicology Network, 1993 [retrieved on Aug. 27, 2012] <http:pmep.cce.cornell.edu/profiles/extoxnet/24d-captan/bentazon-ext.html pp. 1-8.
Disclosed Anonymously 462055:"2-(2,2-difluoroethoxy)-6-trifluoromethy1-N-(5,8-dimethoxy[1,2,4]triazolo[1,5-c]pyrimidin-2-y1)benzenesflufonamide and its use as a herbicide in mixtures", Research Disclosure, Oct. 2002, pp. 1832-1833.
Penoxsulam and its use as a Herbicide in Mixtures for Use in Rice, Wheat, Barley, Oats, Sorghum, Corn, Maize, Ivm, Rangeland Pastures, Grassland, Fallowland, Turf, and Aquatics. The IP.com journal 2005, 5(4), pp. 286-293.
Herbicide Reaction to the Similar Weed Species and Database of Herbicide. <http://www.naas.go.kr/>, no date provided Apr. 3, 2017.
Shi Mingwang and Gao Yangfan, Guidelines to Safe Application of Customary Agrochemicals, Beijing: Chemical Industry Press, Feb. in 2011, pp. 499, 500, and 509, and the English translation.

* cited by examiner

*Primary Examiner* — John Pak
*Assistant Examiner* — Andriae M Holt
(74) *Attorney, Agent, or Firm* — Michael R. Asam; Meunier Carlin & Curfman, LLC

(57) ABSTRACT

A synergistic mixture of penoxsulam and bentazon controls weeds in crops, especially rice and other cereal and grain crops, pastures, rangelands, IVM and turf. In addition to providing improved post-emergence herbicidal weed control, the mixture safens damage to rice.

15 Claims, No Drawings

SYNERGISTIC HERBICIDAL COMPOSITION CONTAINING PENOXSULAM AND BENTAZON

CROSS REFERENCE TO RELATED APPLICATIONS

This application is a continuation of U.S. application Ser. No. 13/219,788, filed Aug. 29, 2011, and claims the benefit of U.S. Provisional Application Ser. No. 61/378,130 filed Aug. 30, 2010.

FIELD OF THE INVENTION

This invention concerns a synergistic herbicidal composition containing (a) penoxsulam and (b) bentazon for controlling weeds in crops, especially rice, cereal and grain crops, pastures, rangelands, industrial vegetation management (IVM), aquatics and turf. These compositions are disclosed as providing improved post-emergence herbicidal weed control and improved safening on rice.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present invention is based on the discovery that penoxsulam and bentazon, already known individually for their herbicidal efficacy, display a synergistic effect when applied in combination.

SUMMARY OF THE INVENTION

The present invention concerns a synergistic herbicidal mixture comprising an herbicidally effective amount of (a) penoxsulam and (b) bentazon. The compositions may also contain an agriculturally acceptable adjuvant and/or carrier.

The present invention also concerns herbicidal compositions for and methods of controlling the growth of undesirable vegetation, particularly in monocot crops including rice, wheat, barley, oats, rye, sorghum, corn, maize, pastures, grasslands, rangelands, fallowland, turf, IVM and aquatics, and the use of these synergistic compositions.

The species spectra of penoxsulam and bentazon, i.e., the weed species which the respective compounds control, are broad and highly complementary. It has now been found that a combination of penoxsulam and bentazon exhibits a synergistic action in the control of rice flatsedge (*Cyperus iria*; CYPIR); arrowhead (*Sagittaria trifolia*; SAGTR); and barnyardgrass (*Echinochloa crus-galli*; ECHCG) at application rates equal to or lower than the rates of the individual compounds. It has also been found that a combination of penoxsulam and bentazon exhibits a safening effect on rice (*Orysa sativa*; ORYSA).

DETAILED DESCRIPTION OF THE INVENTION

Bentazon is the common name for 3-(1-methylethyl)-1H-2,1,3-benzothiadiazin-4(3H)-one 2,2-dioxide. Its herbicidal activity is described in *The Pesticide Manual*, Fifteenth Edition, 2009. Bentazon controls a wide range of economically important broadleaf and sedge weeds. It can be used as the acid itself or as an agriculturally acceptable salt or ester. Use as a salt is preferred, with the sodium salt being most preferred. Bentazon is also known as bentazone and bendioxide.

Penoxsulam is the common name for 2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in *The Pesticide Manual*, Fifteenth Edition, 2009. Penoxsulam controls *Echinochloa* spp., as well as many broadleaf, sedge and aquatic weeds in rice, and *Apera* spp. grass in cereals, as well as many broadleaf weeds in aquatics, many cereal crops, range and pasture, IVM and turf.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant, to the locus of the plant at any stage of growth or before planting or emergence or after emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of bentazon-sodium to penoxsulam at which the herbicidal effect is synergistic lies within the range of between about 13:1 and about 667:1. The rate at which the synergistic composition is applied will depend upon the particular type of weed to be controlled, the degree of control required, and the timing and method of application. In general, the composition of the invention can be applied at an application rate of between about 303 grams per hectare (g/ha) and about 2050 g/ha based on the total amount of active ingredients in the composition. Penoxsulam is applied at a rate between about 3 g/ha and about 50 g/ha and bentazon is applied at a rate between about 300 g/ha and about 2000 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 2,4-D, acetochlor, acifluorfen, aclonifen, AE0172747, alachlor, ametryn, amidosulfuron, aminocyclopyrachlor, aminopyralid, aminotriazole, amitrol, ammonium thiocyanate, anilifos, asulam, atrazine, azimsulfuron, beflubutamid, benazolin, benefin, benfuresate, bensulfuron, bensulide, benthiocarb, benzobicyclon, benzofenap, bifenox, bispyribac, bromacil, bromobutide, bromoxynil, butachlor, butafenacil, butralin, cafenstrole, carbetamide, carfentrazone, chlorflurenol, chlorimuron, chlormequat, chlorpropham, chlortoluron, cinidon, cinosulfuron, clethodim, clodinafop, clomazone, clomeprop, clopyralid, cloransulam, cumyluron, cyanazine, cyclosulfamuron, cycloxydim, cyhalofop, daimuron, dicamba, dichlobenil, dichlorprop, diclofop, diclosulam, diflufenican, diflufenzopyr, dimefuron, dimepiperate, dimethametryn, dimethenamid, dimethenamid, diquat, dithiopyr, diuron, EK2612, EPTC, erioglaucine, esprocarb, ET-751, ethofumesate, ethoxysulfuron, ethbenzamide, etobenzanid, F7967, fenoxaprop, fentrazamide, flazasulfuron, florasulam, fluazifop, flucarbazone, flucetosulfuron (LGC-42153), flufenacet, flufenpyr, flumetsulam, flumiclorac, flumioxazin, fluometuron, flupyrsulfuron, fluroxypyr, flurtamone, fosamine, fomesafen, foramsulfuron, fumiclorac, glufosinate, glyphosate, halosulfuron, haloxyfop, hexazinone, imazamethabenz, imazamox, imazapic, imazapyr, imazaquin, imazethapyr, imazosulfuron, indanofan, indaziflam, iodosulfuron, ioxynil, ipfencarbazone (HOK-201), IR 5790, isoproturon, isoxaben, isoxaflutole, KUH-071, lactofen, linuron, MCPA, mecoprop, mefenacet, mesosulfuron, mesotrione, metamifop, metazosulfuron (NC-620), metolachlor, metosulam, metribuzin, metsulfuron, molinate, monosulfuron, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, pinoxaden, piperophos, pretilachlor, primisulfuron, prodiamine, profluazol, profoxydim, prohexadione, prometon, pronamide, propachlor, propanil, propisochlor, propoxycarbazone, propyrisulfuron (TH-547), propyzamide, prosulfocarb, prosulfuron, pyrabuticarb, pyraclonil, pyraflufen, pyrazogyl, pyrazolynate, pyrazosulfuron, pyrazoxyfen, pyribenzoxim (LGC-40863), pyridate, pyriftalid, pyriminobac, pyrimisulfan (KUH-021), pyrithiobac, pyroxasulfone (KIH-485), pyroxsulam, quinclorac, quinmerac, quinoclamine, quizalofop, rimsulfuron, S-3252, saflufenacil, sethoxydim, simazine, simetryne, SL-0401, SL-0402, sulcotrione, sulfentrazone, sulfometuron, sulfosate, sulfosulfuron, tebuthiuron, tefuryltrione (AVH-301), terbacil, thenylchlor, thiazopyr, thiencarbazone, thifensulfuron, thiobencarb, topramezone, tralkoxydim, triasulfuron, tribenuron, triclopyr, trifloxysulfuron, trifluralin, trinexapac, tritosulfuron and salts, esters, optically active isomers and mixtures thereof.

The synergistic composition of the present invention can, further, be used in conjunction with glyphosate, glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

The synergistic mixture of penoxsulam and bentazon of the present invention also provides a safening effect when applied to rice.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.1 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before making a postemergence, foliar application to exposed weed and crop foliage, or applied as a dry or liquid formulation directly into flooded rice fields. The diluted compositions usually applied as a postemergence, foliar application to weeds or the locus of weeds generally contain 0.25 to 20 weight percent active ingredient and preferably contain 0.4 to 14 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

Evaluation of Postemergence Herbicidal Activity of Mixtures in the Greenhouse

Seeds of the desired test plant species were planted in 80% mineral soil/20% grit planting mixture, which typically has a pH of 7.2 and an organic matter content of approximately 3 percent, in plastic pots with a surface area of 128 square centimeters ($cm^2$). The growing medium was steam sterilized. The plants were grown for 7-19 days (d) in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were treated with postemergence foliar applications when they reached the second to fourth true leaf stage. All treatments were applied using a randomized complete block trial design, with 4 replications per treatment.

Treatments consisted of the compounds as listed in Tables 1 and 3, each compound applied alone and in combination. Formulated amounts of penoxsulam and bentazon, were placed in 60 milliliter (mL) glass vials and dissolved in a volume of 60 mL of a water solution containing Agri-dex crop oil concentrate in a 1% v/v ratio. Compound requirements are based upon a 12 mL application volume at a rate of 187 liters per hectare (L/ha). Spray solutions of the mixtures were prepared by adding the stock solutions to the appropriate amount of dilution solution to form a 12 mL spray solution with active ingredients in single and two way combinations. Formulated compounds were applied to the plant material with an overhead Mandel track sprayer equipped with 8002E nozzles calibrated to deliver 187 L/ha at a spray height of 18 inches (43 centimeters (cm)) above average plant canopy.

The treated plants and control plants were placed in a greenhouse as described above and watered by sub-irrigation to prevent wash-off of the test compounds. Treatments were rated at 7 to 21 d after application as compared to the untreated control plants. Visual weed control was scored on a scale of 0 to 100 percent where 0 corresponds to no injury and 100 corresponds to complete kill.

Evaluation of Postemergence Herbicidal Activity of Mixtures in the Field

Field trials were conducted in rice using standard herbicide small plot research methodology. Plots varied from 3×3 meter (m) to 3×10 m (width×length) with 4 replicates per treatment. The rice crop was grown using normal cultural practices for fertilization, seeding, watering, flooding and maintenance to ensure good growth of the crop and the weeds.

All treatments in the field trials were applied using a $CO_2$ backpack sprayer calibrated to apply 187 L/ha spray volume. Commercially available products of penoxsulam and bentazon were mixed in water at appropriate formulated product rates to achieve the desired rates based on a unit area of application (hectare) to achieve the desired rates as shown. Treatments were rated at 6 to 45 d after application as compared to the untreated control plants. Visual weed control was scored on a scale of 0 to 100 percent where 0 corresponds to no injury and 100 corresponds to complete kill.

Tables 1 and 2 demonstrate the herbicidal synergistic efficacy of penoxsulam+bentazon-sodium tank mixes on weed control. Table 3 demonstrates the herbicidal synergistic safening of two crops to mixtures of penoxsulam+bentazon-sodium. All treatment results, both for the single product and mixtures, are an average of 3 to 4 replicates and the tank mix interactions are significant at the P>0.05 level.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 1-3. All comparisons are an average of 3 to 4 replicates and are significant at the P>0.05 level.

TABLE 1

Synergistic Activity of Herbicidal Compositions on Sedge Weeds (*Cyperus iria*; CYPIR) in the Greenhouse at 21 Days after Application

| Application Rate (g/ha) | | % Control | |
| --- | --- | --- | --- |
| | | CYPIR | |
| Penoxsulam | Bentazon-Sodium | Ob | Ex |
| 3 | 0 | 20 | |
| 0 | 500 | 55 | |
| 3 | 500 | 85 | 64 |
| 3 | 0 | 20 | |
| 0 | 1000 | 72 | |
| 3 | 1000 | 98 | 78 |

TABLE 2

Synergistic Activity of Herbicidal Compositions on Broadleaf and Grass Weeds *Sagittaria trifolia* (SAGTR) and *Echinochloa crus-galli* (ECHCG) in the Field at 6 to 45 Days after Application

| Application Rate (g/ha) | | % Control | | | |
| --- | --- | --- | --- | --- | --- |
| | | SAGTR | | ECHCG | |
| Penoxsulam | Bentazon-Sodium | Ob | Ex | Ob | Ex |
| 15 | 0 | 38 | — | — | — |
| 0 | 1100 | 78 | — | — | — |
| 15 | 1100 | 100 | 87 | — | — |
| 23 | 0 | 45 | — | — | — |
| 0 | 1100 | 78 | — | — | — |
| 23 | 1100 | 100 | 88 | — | — |
| 38 | 0 | — | — | 30 | — |
| 0 | 2000 | — | — | 0 | — |
| 38 | 2000 | — | — | 53 | 30 |

TABLE 3

Activity of Herbicidal Compositions on Safening of Injury in Rice (ORYSA) in the Greenhouse at 21 Days after Application

| Application Rate (g/ha) | | % Control | |
| --- | --- | --- | --- |
| | | ORYSA | |
| Penoxsulam | Bentazon-sodium | Ob | Ex |
| 7.5 | 0 | 0 | — |
| 0 | 500 | 14 | — |
| 7.5 | 500 | 2.5 | 14 |
| 15 | 0 | 0 | — |
| 0 | 500 | 14 | — |
| 15 | 500 | 0 | 14 |
| 7.5 | 0 | 0 | — |
| 0 | 1000 | 16 | — |
| 7.5 | 1000 | 0 | 16 |
| 15 | 0 | 0 | — |
| 0 | 1000 | 16 | — |
| 15 | 1000 | 0 | 16 |

What is claimed is:

1. A synergistic herbicidal mixture comprising an herbicidally effective amount of (a) penoxsulam and (b) bentazon, or an agriculturally acceptable salt or ester thereof, wherein the weight ratio of bentazon, or an agriculturally acceptable salt or ester thereof, to penoxsulam is in the range of from about 133:1 to about 333:1.

2. The synergistic herbicidal mixture of claim 1 comprising an agriculturally acceptable salt of bentazon.

3. The synergistic herbicidal mixture of claim 2 in which the agriculturally acceptable salt of bentazon is the sodium salt.

4. The synergistic herbicidal mixture of claim 1 in which the weight ratio of bentazon, or an agriculturally acceptable salt or ester thereof, to penoxsulam is in the range of from about 167:1 to about 333:1.

5. An herbicidal composition comprising an herbicidally effective amount of the synergistic herbicidal mixture of claim 1 and an agriculturally acceptable adjuvant and/or carrier.

6. A method of controlling undesirable vegetation which comprises contacting the vegetation or the locus thereof with or applying to the soil or water to control the emergence or growth of vegetation an herbicidally effective amount of the synergistic herbicidal mixture of claim 1.

7. The method of claim 6, wherein the undesirable vegetation is controlled in rice, wheat, barley, oats, rye, sorghum, corn, maize, cereal crops, grain crops, pastures, rangelands, grasslands, fallowland, IVM, aquatics or turf.

8. The method of claim 6, wherein the synergistic herbicidal mixture is applied at an application rate of between about 303 grams per hectare (g/ha) and about 2050 g/ha based on the total amount of active ingredients in the composition.

9. The method of claim 6, wherein the undesirable vegetation is a *Cyperus, Sagittaria*, or *Echinochloa* plant.

10. The method of claim 9, wherein the undesirable vegetation is *Cyperus iria, Sagittaria trifolia*, or *Echinochloa crus-galli*.

11. The method of claim 6, wherein the synergistic herbicidal mixture is applied post-emergence.

12. The method of claim 6, wherein the undesirable vegetation is controlled in rice.

13. The method of claim 12, wherein the rice is *Orysa sativa*.

14. The method of claim 6, which comprises contacting the vegetation to control the emergence or growth of vegetation an herbicidally effective amount of (a) penoxsulam and (b) bentazon, or an agriculturally acceptable salt or ester thereof.

15. The method of claim 6, wherein the weight ratio of bentazon, or an agriculturally acceptable salt or ester thereof, to penoxsulam is in the range of from 167:1 to 333:1.

* * * * *